United States Patent
Sternlicht et al.

(10) Patent No.: US 11,495,338 B1
(45) Date of Patent: Nov. 8, 2022

(54) METHODS AND SYSTEMS FOR REDISTRIBUTING MEDICATION

(71) Applicant: MEDICIRCLE INC.

(72) Inventors: Eliza Sternlicht, Providence, RI (US); Jack Schaeffer, Wyckoff, NJ (US)

(73) Assignee: MEDICIRCLE INC.

( * ) Notice: Subject to any disclaimer, the term of this patent is extended or adjusted under 35 U.S.C. 154(b) by 0 days.

(21) Appl. No.: 17/575,792

(22) Filed: Jan. 14, 2022

(51) Int. Cl.
*G16H 20/10* (2018.01)
*G16H 70/40* (2018.01)
*G16H 50/20* (2018.01)

(52) U.S. Cl.
CPC ............ *G16H 20/10* (2018.01); *G16H 50/20* (2018.01); *G16H 70/40* (2018.01)

(58) Field of Classification Search
CPC ......... G16H 20/10; G16H 50/20; G16H 70/40
See application file for complete search history.

(56) References Cited

U.S. PATENT DOCUMENTS

| 9,811,782 | B1 | 11/2017 | Miceli |
| 9,892,433 | B2 | 2/2018 | Kircher |
| 9,940,439 | B2 | 4/2018 | Royaee |
| 2005/0096941 | A1 | 5/2005 | Tong |
| 2011/0257991 | A1 | 10/2011 | Shukla |
| 2013/0226600 | A1 | 8/2013 | Barfield |
| 2015/0221001 | A1* | 8/2015 | Kircher ............ G06Q 30/0279 705/2 |

FOREIGN PATENT DOCUMENTS

| WO | 2020168018 | 8/2020 |
| WO | 2020206154 | 10/2020 |
| WO | 2021216910 | 10/2021 |

\* cited by examiner

*Primary Examiner* — Michael Tomaszewski
*Assistant Examiner* — Mohmad Muqueeth
(74) *Attorney, Agent, or Firm* — Caldwell Intellectual Property Law

(57) ABSTRACT

A system for redistributing medication including a computing device configured to receive a communication regarding a medication donation from a donor, wherein the communication includes donor medication information regarding the medication donation. The computing device further configured to verify the medication donation including verifying the identity of the donated medication. Verifying the identity of the donated medication includes collecting actual medication information. The computing device also configured to enter final medication information corresponding to the medication donation into the medication database. The computing device configured to match the donated medication to a recipient selected from a recipient database as a function of a set of associated recipient data.

20 Claims, 11 Drawing Sheets

METHODS AND SYSTEMS FOR REDISTRIBUTING MEDICATION

FIELD OF THE INVENTION

The present invention generally relates to the field of medication management. In particular, the present invention is directed to methods and systems for redistributing medication.

BACKGROUND

It is important to medical treatment to ensure that patients are able to receive the correct medication when they need it. If the patient is not able to receive the correct medication, it may have dire consequences for their health. Thus, unused medication represents wasted potential, where the unused medication could be more useful if it was being used to treat a patient in need. Existing solutions for redistributing medication do not adequately resolve this problem.

SUMMARY OF THE DISCLOSURE

In an aspect, a system for redistributing medication, the system including a computing device designed and configured to receive a communication regarding a medication donation from a donor, wherein the communication includes donor medication information regarding the medication donation. The computing device further designed and configured to verify the medication donation wherein verifying the medication donation includes verifying the identity of the donated medication. Verifying the identity of the donated medication includes collecting actual medication information from the medication donation. The computing device also designed and configured to enter final medication information corresponding to the medication donation into the medication database. The computing device additionally designed and configured to match the donated medication to a recipient selected from a recipient database as a function of a set of recipient data, wherein each recipient in the recipient database has an associated set of recipient data.

In another aspect, a method for redistributing medication, the method including receiving a communication regarding a medication donation from a donor, wherein the communication includes donor medication information regarding the medication donation. The method further including verifying the medication donation, wherein verifying the medication donation includes verifying the identity of the medication donation. Verifying the identity of the donated medication includes collecting actual medication information from the medication donation. The method also further including entering final medication information corresponding to the medication donation into the medication database. The method additionally including matching the medication donation to a recipient selected from a recipient database as a function of a set of recipient data, wherein each recipient in the recipient database has an associated set of recipient data.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for redistributing medicine. In an embodiment, recipients from a recipient database may be matched to medication donation. In some embodiments, this may involve a matching machine learning model. This matching may be based on, for example, recipient data from the recipient database.

Aspects of the present disclosure can be used to verifying medication donations. Aspects of the present disclosure can also be used verify the identity of a medication donation. This may be done for example, using a machine learning algorithm. In some embodiments, a pharmacist may verify the identity of the medication donation. In some aspects of the present disclosure, verifying medication donations may include verifying the integrity of a medication donation.

Aspects of the present disclosure allow for a verification record to be stored using an immutable sequential listing. This bolsters the integrity of the verification record as it makes it harder for the verification record to be falsified or otherwise tampered with.

Figure 1:
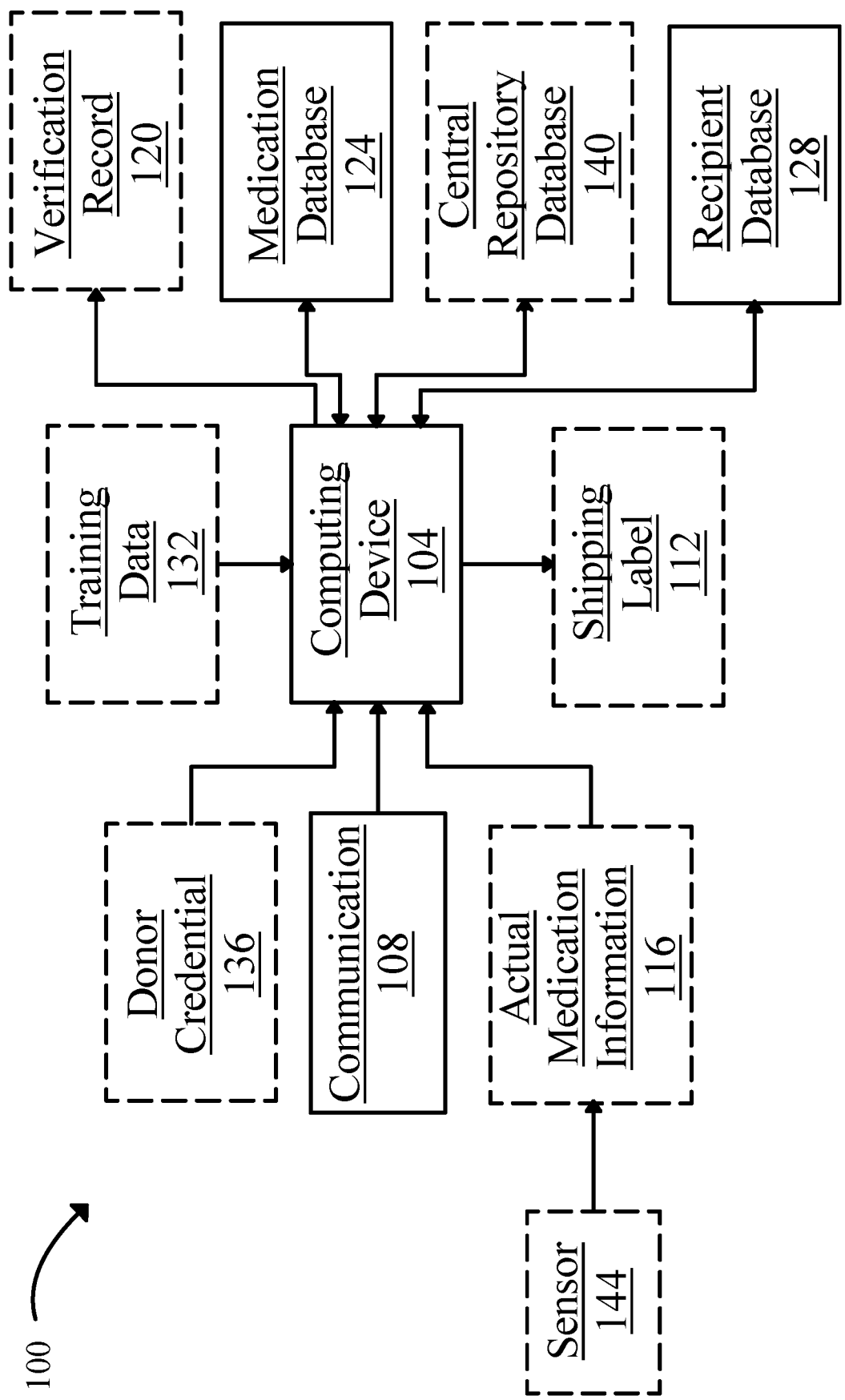
FIG. 1 is a diagram of a system for redistributing medication.

Referring now to FIG. 1, a system for redistributing medication 100 is shown. System 100 includes a computing device 104. System includes a computing device. computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device may include a single computing device operating independently, or may include two or more computing device operating in concert, in parallel, sequentially or the like; two or more computing devices may be included together in a single computing device or in two or more computing devices. computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device may include but is not limited to, for example, a computing device or cluster of computing devices in a first location and a second computing device or cluster of computing devices in a second location. computing device may include one or more computing devices dedicated to data storage, security, distribution of traffic for load balancing, and the like. computing device may distribute one or more computing tasks as described below across a plurality of computing devices of computing device, which may operate in parallel, in series, redundantly, or in any other manner used for distribution of tasks or memory between computing devices. computing device may be implemented using a "shared nothing" architecture in which data is cached at the worker, in an embodiment, this may enable scalability of system 100 and/or computing device.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured and arranged to receive a communication 108 regarding a medication donation from a donor. Communication 108 may be received via wireless or wired communication. As non-limiting examples, wireless communication may be WiFi, cellular data, 3G, 4G, 5G, LTE, radio communication, satellite communication, and the like. Communication 108 may contain a variety of information regarding the medication donation. In an embodiment, communication 108 may contain information about the law such as appropriate medication dispensing laws, appropriate medication storage information, appropriate medical record information, appropriate pharmacy regulations, legislation and/or rules that authorize repurposing and/or donating medications, and the like. In an embodiment, communication 108 may contain donor medication information concerning the medication in the medication donation. As non-limiting example, this information may include quantity of medication, type of medication, expiration date of medication, brand of medication, and the like. In some embodiments, communication 108 may contain geographic information regarding the medication donation. As non-limiting examples, this may include the state where the medication donation is, the organization that has possession of the medication donation, the individual who has possession of the medication donation, the address of the location of the medication donation, and the like. In some embodiments, communication 108 may include donor information. As non-limiting examples, this may include, the name of the donor, the age of the donor, whether the donor is an institutional donor, and the like. One of ordinary skill in the art, after having reviewed the entirety of this disclosure, would appreciate that communication 108 may include a variety of information concerning the medication donation. For the purposes of this disclosure, a "medication donation" is a portion, part, or group of unused medication that is to be redistributed. For the purposes of this disclosure, "medication" is a drug used to prevent, cure, treat, diagnose, alleviate, or contain a disease, symptoms, conditions, or nutritional deficiency. As a non-limiting example, medication may include blood pressure medications, such as Valsartan, Metoprolol, Olmesartan, and the like. As another non-limiting example, medication may include high-cholesterol medication, such as Atorvastatin, Fluvastatin, Lovastatin, and the like. As another non-limiting example, medication may include various types of vitamins, such as Vitamin D, a multivitamin, Vitamin B3, Calcium, and the like. As another non-limiting embodiment, medication may include immunizations, such as an influenza vaccine, an MMR combined vaccine, a COVID-19 vaccine, and the like. As another non-limiting example, medication may include preventative medications, such as Atovaquone-proguanil. In some embodiments, a single medication may include one or more active ingredients. In some embodiments, medication may include a medication regimen, including more than one medication. For the purposes of this disclosure a "donor" is the person or entity that is disposing of, donating, or selling the medication donation. In some embodiments, the donor may receive compensation for the medication donation. In some other embodiments, the donor may receive no compensation for the medication.

With continued reference to FIG. 1, in some embodiments, computing device 104 may be designed and configured to generate a shipping label 112 for the medication donation. In some embodiments, generating a shipping label 112 for the medication donation may be a part of receiving a communication regarding a medication donation from a donor. In some embodiments, shipping label 112 may be generated automatically, for example, as a result of computing device 104 receiving communication 108. In some embodiments, shipping label 112 may be generated as a result of a command from donor, or from any user of computing device 104. Shipping label 112 may contain a variety of information; for example, an address, a return address, a barcode, and the like. Generating shipping label 112 may include interfacing with a third-party application programming interface (API). In some embodiments, generating shipping label 112 may include sending shipping label 112 to the donor. As a non-limiting example, sending shipping label 112 to the donor may include sending shipping label 112 using a postal service, parcel service, or currier service. As a non-limiting example, sending shipping label 112 to the donor may include sending the shopping label (or a link to shipping label 112) by electronic means; for example, email, instant message, social media message, Short Message Service (SMS), Multimedia Messaging Service (MMS), Bluetooth, and the like.

With continued reference to FIG. 1, computing device 104 is designed and configured to verify the medication donation wherein verifying the medication donation includes verifying the identity of the medication donation. Verifying the identity of the medication donation includes collecting actual medication information 116 from the medication donation. Actual medication information 116 may include any information collected from the medication donation itself. As a non-limiting example, actual medication information may include data collected from the medication donation, such as chemical composition, shape, color, strength, expiration date, efficacy, dosages left, and the like. As a non-limiting example, actual mediation information may include records, such as images or videos, of the medication donation. Images and videos of the medication donation, as non-limiting examples, may be of the medication donation packaging, a pill of the medication donation, a unit of the medication donation, a dose of the medication donation, and the like.

Continuing to refer to FIG. 1, verifying the identity of the medication donation may include using an identification machine learning model to verify the identity of the medication donation. The identification machine learning model may be trained to verify the identity of the medication donation by comparing the donor medication information in communication with the actual medication information 116. For the purposes of this disclosure, the "identity of the medication donation" refers to the generic name, brand name, quantity of medication, dosage of medication, or chemical composition of the medication. In some embodiments, identification machine learning model may output a donation identity verification. In some embodiments, the donation identity verification may be a binary value. As a non-limiting example, "0" may represent a failed verification, whereas "1" may represent a successful verification. In some embodiments, donation identity verification may represent a confidence in the verification. Identification machine learning model may be implemented using a machine learning module, as discussed in this disclosure.

Continuing to refer to FIG. 1, in some embodiments, verifying the medication donation may include verifying the integrity of the medication donation. For the purposes of this disclosure, the "integrity" of the medication donation, refers to whether or not the medication donation is still suitable for its intended purpose. As a non-limiting example, this may include chemical integrity. As a non-limiting example verifying the integrity of the medication donation may include verifying that the chemical content of the medication donation is proper. As a non-limiting example, a medication donation may no longer be suitable for its intended purpose is it has expired. As another non-limiting example, a medication may no longer be suitable for its intended purpose if it has been tampered with. In some embodiments, verifying the integrity of the medication donation may include receiving an inspection report from a pharmacist. For the purposes of this disclosure, a "pharmacist" is a health professional that provides pharmaceutical care and/or services. In some embodiments, the pharmacist, in preparing the report, may certify intact tamper evident seals and check the expiration date. In some embodiments, the inspection report may also verify the identity of the medication donation. For example, the pharmacist may inspect each pill in the medication donation, verify drug identity, and check correct dosage.

With continued reference to FIG. 1, verifying the medication donation may further include selecting, optionally, the medication donation for further verification testing. In an embodiment, "selecting, optionally, the medication donation" may include randomly selecting certain medication donations. As a non-limiting example, this may be accomplished using the output of a random number generator. By changing what output from the random number generator causes the medication donation to undergo further verification testing, the probability of a given medication donation being selected can be adjusted. In some embodiments, "selecting, optionally, the medication donation" may include selecting every $n^{th}$ medication donation, wherein n is an integer above zero. As a non-limiting example, where n=100 every $100^{th}$ medication donation may be selected for further verification testing. In some embodiments, a statistically relevant sample of medication donations may be selected for further verification testing. As a non-limiting example, a statistically relevant sample of medication donation may be selected for further verification testing, as a proxy for selecting all of the medication donations for further verification testing. For the purposes of this disclosure, a sample is "statistically relevant" if the sample is large enough that, under the principles of statistics, the properties of the sample can reasonably be extrapolated to the whole. In some embodiments, further verification testing may include further chemical testing. In some embodiments, selecting, optionally, the medication donation for further verification testing may include sending the medication donation to a third-party chemical analytic company.

With continued reference to FIG. 1, in some embodiments, verifying the medication donation may comprise creating a verification record 120 including a verification status of the medication donation, wherein the verification record 120 is sored using an immutable sequential listing. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered. The verification record 120 may include a plurality of entries for a plurality of medication donations. In some embodiments, the verification record 120 may include additional information regarding the medication donation. As a non-limiting example, the verification record 120 may also include a verification failure reason. The verification failure reason may be a reason why the medication donation failed verification. As a non-limiting example, this may include that the medication donation had expired, or that the medication donation did not match the donor medication information from communication 108. A person of ordinary skill in the art, having reviewed the entirety of this disclosure, would realize that there is a variety of additional information regarding the medication donation may be included in the verification record 120. The concept of an immutable sequential listing is discussed further with respect to FIG. 7.

With continued reference to FIG. 1, computing device 104 is designed and configured to enter final medication information corresponding to the medication donation into the medication database 124. In some embodiments, final medication information my include a combination of data from the donor medication information and actual medication information 116. In some embodiments, final medication information may include at least a portion of actual medication information 116. In some embodiments, medication database 124 may be a database with entries corresponding to each medication donation. As a non-limiting example, each entry corresponding to a medication donation may be associated with one or more components corresponding to one or more data categories. The one or more data categories may include any category of data included in donor medication information or actual medication information 116. In some embodiments, medication database 124 may include entries for a plurality of types of medication. As a non-limiting example, in these embodiments, a "type of medication" may be the generic name for the medication. In these embodiments, the corresponding components of a plurality of final medication information corresponding to the same type of medication, may be concatenated together. Medication database 124 may be implemented, without limitation, as a relational database, a key-value retrieval database such as a NOSQL database, or any other format or structure for use as a medication database 124 that a person skilled in the art would recognize as suitable upon review of the entirety of this disclosure. Medication database 124 may alternatively or additionally be implemented using a distributed data storage protocol and/or data structure, such as a distributed hash table or the like. Medication database 124 may include a plurality of data entries and/or records as described above. Data entries in a medication database 124 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a medication database 124 may store, retrieve, organize, and/or reflect data and/or records as used herein, as well as categories and/or populations of data consistently with this disclosure. In some embodiments, a credential may be required in order for computing device 104 to access the medication database 124. As non-limiting examples, a credential may include a license, authority, digital credential, password, certificate, and the like.

Still referring to FIG. 1, system 100 may include a recipient database 128. Recipient database 128 may include a plurality of entries for a plurality of recipients for medication donations. Each entry for a recipient may include an associated set of recipient data. "Recipient data," for the purposes of this disclosure is data corresponding to a recipient. Recipient database 128 may be implemented, without limitation, as a relational database, a key-value retrieval database such as a NOSQL database, or any other format or structure for use as a database that a person skilled in the art would recognize as suitable upon review of the entirety of this disclosure. Recipient database 128 may alternatively or additionally be implemented using a distributed data storage protocol and/or data structure, such as a distributed hash table or the like. Recipient database 128 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. In some embodiments, a credential may be required in order for computing device 104 to access the recipient database 128. As non-limiting examples, a credential may include a license, authority, digital credential, password, certificate, and the like.

Still referring to FIG. 1, in some embodiments, system 100 may include a public medication database. The public medication database may include medication information corresponding to medication donations. The public medication database may be publicly accessible, meaning that a member of the public can access and browse the database. In some embodiments, a member of the public may need to register in order to view the public database. As a non-limiting example, a member of the public may need to create a username and password in order to view the public database. In other embodiments, the public database may be accessible to members of the public regardless of whether or not they have registered. Public medication database may be implemented, without limitation, as a relational database, a key-value retrieval database such as a NOSQL database, or any other format or structure for use as a database that a person skilled in the art would recognize as suitable upon review of the entirety of this disclosure. Public medication database may alternatively or additionally be implemented using a distributed data storage protocol and/or data structure, such as a distributed hash table or the like. Public medication database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, computing device 104 may be designed and configured to match the medication donation to a recipient selected from recipient database 128 as a function of a set of recipient data, wherein each recipient in the recipient database 128 has an associated set of recipient data. In some embodiments, computing device 104 may perform this matching process by isolating a particular component of the set of recipient data. As a non-limiting example, where a component of the set of recipient data is the quantity of medication remaining for the associated recipient, computing device 104 may match the medication donation to the recipient with the lowest quantity of medication remaining. In some embodiments, computing device 104 may perform this matching process by assigning weights to certain components in the set of recipient data and matching the medication donation to the recipient with the highest combined value of the weighted components. In some embodiments, the match of the medication donation and the recipient may be stored in recipient database 128. As a non-limiting example, the match may be stored as a component of the recipient data in recipient database 128.

With continued reference to FIG. 1, in some embodiments, computing device 104 may be designed and configured to match the medication donation to a recipient selected from recipient database 128 using a matching machine learning model, wherein the matching machine learning model that takes medication information from the medication database as input and outputs at least a recipient from the recipient database. In some embodiments, computing device 104 may be designed and configured to train the machine learning model using training data 132. Matching machine learning model may be implemented using a machine learning module, as described in this disclosure. In some embodiments, matching machine learning module may be a neural network. Neural networks are discussed further with respect to FIGS. 8 and 9. "Training data," as used herein, is data containing correlations that a machine-learning process, such as a classifier, may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Training data 132 may include, in some embodiments, prior purchasing data for recipients, prior medication purchasing data, prior medication prescribing data, prior medication need data, and the like.

With continued reference to FIG. 1, computing device 104 may be designed and configured to remove the medication donation information corresponding to a medication donation from the medication database 124 when a buffer time period before an expiration date of the medication donation is reached. In some embodiments, buffer time period may include any number above and including zero. In some embodiments, buffer time period may be an expressed in a unit of time; such as, for example, seconds, minutes, hours, days, weeks, months, years, and the like. As a non-limiting example, where the buffer time period is two weeks, computing device 104 may be designed and configured to remove the medication donation information corresponding to a medication donation from the medication database 124 two weeks before the expiration date of the medication donation. For the purposes of this disclosure, an "expiration date" is a previously determined date, after which the item having the expiration date should no longer be used. As another non-limiting example, where the buffer time period is zero days, the medication donation may be removed from medication database 124 by computing device 104 on the expiration date associated with that medication donation. In some embodiments, buffer time period may apply globally to all medication donations. In some embodiments, buffer time period may be set on an individual basis for each medication donation. In some embodiments, buffer time period may be set on an individual basis for each type of medication.

Still referring to FIG. 1, in some embodiments, computing device 104 may be designed and configured to verify the identity of the donor using at least a donor credential 136 from the donor. In some embodiments, computing device may be configured to receive a donor credential 136. For the purposes of this disclosure, a "credential" is an item used to establish a person or entity's identity or qualifications. As a non-limiting example, donor credential 136 may include a password, passcode, secret phrase, or the like. As another non-limiting example, donor credential 136 may include a form of identification, such as an ID card, passport, driver's license, and the like. As another non-limiting example, donor credential 136 may include a certification document, showing that donor is certified to be a medication donor. In some embodiments, credential may be a string of characters, in other embodiments, it may be a picture or scan of a physical credential. Computing device 104 may use a machine learning algorithm that takes as input images, pdfs, pngs, and the like and outputs an identity verification result. In some embodiments, computing device 104 may accomplish this using a machine learning module, as discussed later in this disclosure. Identity verification result may be a binary value indicating whether identity verification was successful or unsuccessful. In some embodiments, identity verification result may be a value indicating the probability that the identity of donor is correct. In some embodiments, computing device 104 may verify the identity of the donor using at least a donor credential 136 using an image classification module, as discussed later in this disclosure. In some embodiments, as part of verifying the identity of the donor, computing device 104 may preform optical character recognition (OCR), using, in some embodiments, an OCR module, as discussed later in this disclosure.

With continued reference to FIG. 1, computing device 104, may be designed and configured to identify a central repository to store the medication donation. For the purposes of this disclosure, a "central repository" is a storage location for medication donations. As a non-limiting example, central repository may be a warehouse, storeroom, depository, stockroom, and the like. In some embodiments, central repository may be part of a larger entity. As a non-limiting example, central location may be part of a hospital. In some embodiments, storage within central repository may be done by an organizational methodology, such as by storing medications in alphabetic order, by brand name, by generic name and the like. In some embodiments, storage may be chaotic and without any organizational methodology. In some embodiments, storage in a virtual repository may mirror and/or be in alignment with a central repository. In some embodiments, computing device 104 may identify a central repository by locating the closest central repository to the medication donation. This may involve, as a non-limiting example, accessing a central repository database 140. Central repository database 140 may, in some embodiments, include entries for a plurality of central repositories. In some embodiments, each central repository entry for the plurality of central repositories may be associated with central repository data pertaining to that central repository. Central repository data may include any data relevant to that central repository. As non-limiting examples, central repository data may include an address for the central repository, the climate of the central repository, the amenities of the central repository, and the like. In some embodiments, computing device may use a central repository machine learning model to identity the central repository. Central repository machine learning model may be implemented using a machine learning module, as discussed in this disclosure. In some embodiments, central repository machine learning model may be a neural network. Neural networks are discussed further with respect to FIGS. 8 and 9. In some embodiments, central repository machine learning model may take as input data from recipient database 128 and/or central repository database 140. In some embodiments, central repository machine learning model may output a central repository identification, wherein the central repository identification includes a central repository. As a non-limiting example, central repository machine learning model may be configured to identify the central repository based on the climate of the central repository (for storing the medication donation) and the demand for the medication donation in the geographic area of the central repository (for example, using recipient database 128). For the purposes of this disclosure, "geographic area" is a demarcated area of the earth. As non-limiting example, geographic area may include a town, a city, a county, a region, a metropolitan area, a city, a state, a country, and the like. In some embodiments, a geographic area may include a circular region surrounding a central repository. For example, a 100-mile region surrounding a central repository. In other embodiments, a geographic area may be defined relative to the positions of all of the central repositories. For example, a first central repository may be part of a geographic area, wherein the geographic area is the area of the earth that is closer to the first central repository than it is to any other central repository. Central repository database 140 may be implemented, without limitation, as a relational database, a key-value retrieval database such as a NOSQL database, or any other format or structure for use as a database that a person skilled in the art would recognize as suitable upon review of the entirety of this disclosure. Central repository database 140 may alternatively or additionally be implemented using a distributed data storage protocol and/or data structure, such as a distributed hash table or the like. Central repository database 140 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, medication donation may undergo an isolation process. In some embodiments, the isolation process may include three steps. In the first step, the medication donation may be held in an isolation area. The isolation area is different from the central repository. As part of the first step, the medication donation may be held in an isolation area until the identity of the medication has been verified. As a non-limiting example, this may include verifying the correct packaging and medication type. As part of the first step, the medication donation may be held in an isolation area until the expiration date of the medication donation has been verified. The isolation process may include a second step, wherein the medication donation is sent to a central repository. In some embodiments, the central repository may be the central repository identified by computing device 104, as discussed above. While at the central repository, the medication donation may undergo further testing such as chemical analysis, inspection by a registered pharmacist, machine vision analysis, or any other medication testing process discussed in this disclosure.

With continued reference to FIG. 1, in some embodiments, system may include a sensor 144. Sensor 144 may be used to collect actual medication information. For the purposes of this disclosure, a "sensor" is a device (or devices) that is configured to detect a phenomenon and transmit information and/or datum related to the detection of the phenomenon. In some embodiments, sensor 144 may include a camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object. In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively, where "image" is used as a verb, in this disclosure, it refers to generation and/or formation of an image. In some embodiments, using the sensor 144 to collect actual medication information 116 may include receiving an image from the camera. As part of collecting actual medication information, in some embodiments, an image classifier may be used by computing device 104 to classify the image transmitted by the camera. Image classifiers are disclosed further with reference to FIG. 2.

With continued reference to FIG. 1, in embodiments where sensor 144 includes a camera, system 100 may include a machine vision system. A machine vision system may use images from at least a camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and ϕ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

With continued reference to FIG. 1, the sensor 144 may include a variety of sensors. For example, sensor 144 may be a scale. As a non-limiting example, sensor 144 may detect the weight of the medication donation and transmit this information to computing device 104 as actual medication information 116. In some embodiments, sensor 144 may include a barcode reader. A "barcode reader," for the purposes of this disclosure, includes a light source, and a light sensor configured to detect optical impulses reflected back from the light source off of the barcode being scanned. The barcode may be consistent with any barcode disclosed in this disclosure. A barcode reader may be configured to read a barcode, such as barcode 404 in FIG. 4, and transmit this information to computing device 104 as actual medication information 116. Sensor 144 may be part of a sensor suite. For example, sensor 144 may include a plurality of sensing devices, such as a camera, a barcode scanner, and/or a scale. A person of ordinary skill in the art would appreciate that a variety of different types of sensors may be included in the sensor suite depending on the exact functionality needed.

Figure 2:
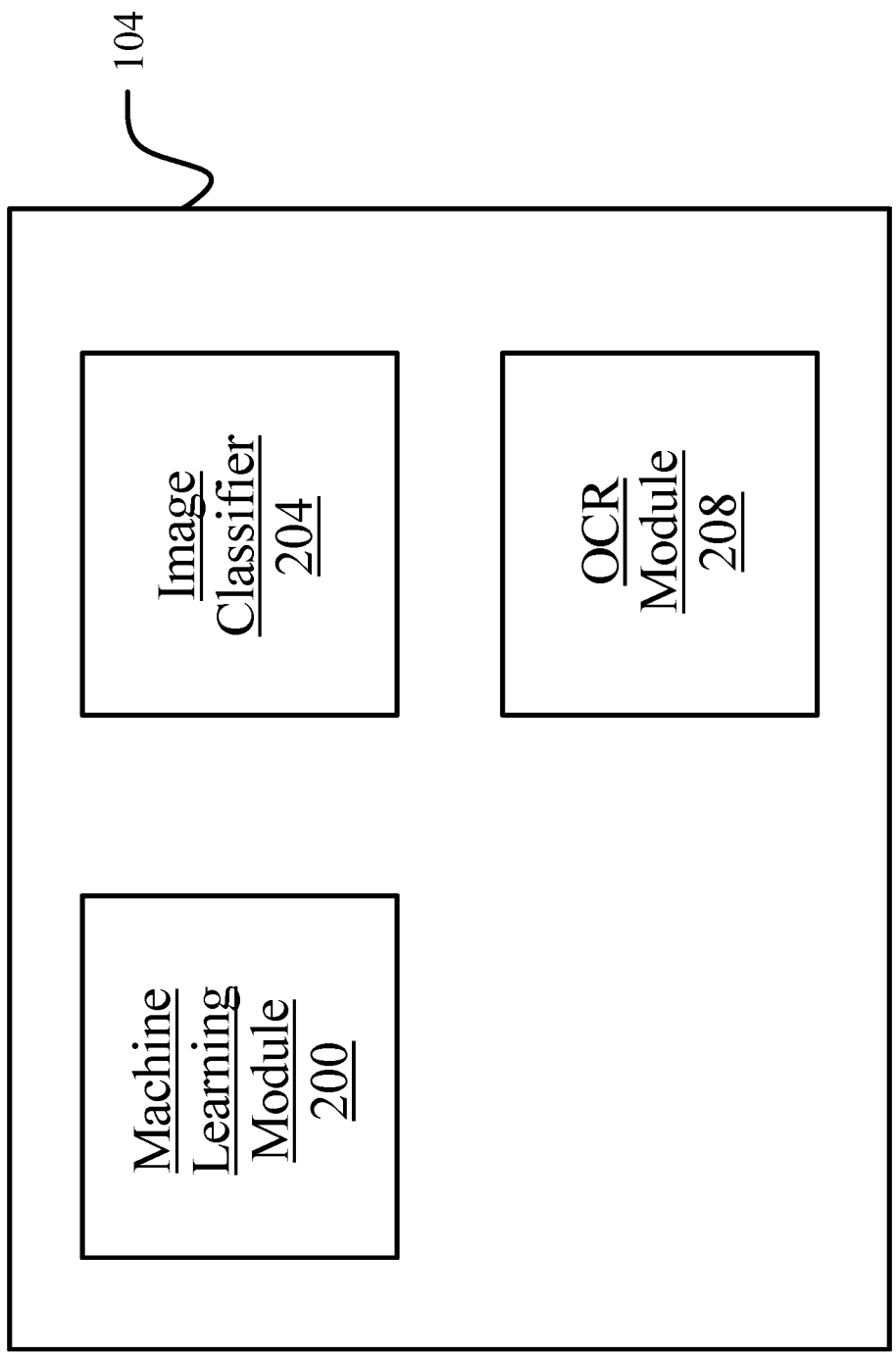
FIG. 2 is a diagram of an exemplary embodiment of a computing device.

Referring now to FIG. 2, FIG. 2 depicts an exemplary embodiment of a computing device 104. Computing device 104 may include a machine learning module 200. Machine learning module may be consistent with machine learning module 1000 discussed with reference to FIG. 10.

Still referring to FIG. 2, computing device 104 may include an image classifier 204. Computing device 104 may be configured to perform image classification using image classifier 204. Image classifier 204 may be communicatively connected to computing device 104. In some embodiments, image classifier 204 may be a component or module of computing device 104. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another computing device may generate a classifier using a classification algorithm, defined as a process whereby a computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, kernel estimation, learning vector quantization, and/or neural network-based classifiers.

Still referring to FIG. 2, image classifier 204 may be generated, as a non-limiting example, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. A computing device may then calculate a likelihood table by calculating probabilities of different data entries and classification labels. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, image classifier 204 may be generated using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 2, in some embodiments, computing device 104 may be configured to train image classifier 204 or any machine learning module (e.g., machine learning module 1000 in FIG. 10 or machine learning module 200) using any classification algorithm described above operating on training data. "Training data," as used herein, is data containing correlations that a machine-learning process, such as a classifier, may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and further referring to FIG. 2, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. Training data used to train image classifier 204 may include a plurality of entries, each including attributes of an image such as a portion of a frame of a plurality of frames, and/or a shape detected therein, which may be used to classify the image to other images in training data.

With continued reference to FIG. 2, computing device 104 may include an OCR module 208. Still refereeing to FIG. 2, in some embodiments, optical character recognition or optical character reader (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 2, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 2, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases. a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 2, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 2, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 1, 2, and 8-10. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, Calif., United States.

Still referring to FIG. 2, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 8 and 9.

Still referring to FIG. 2, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Figure 3:
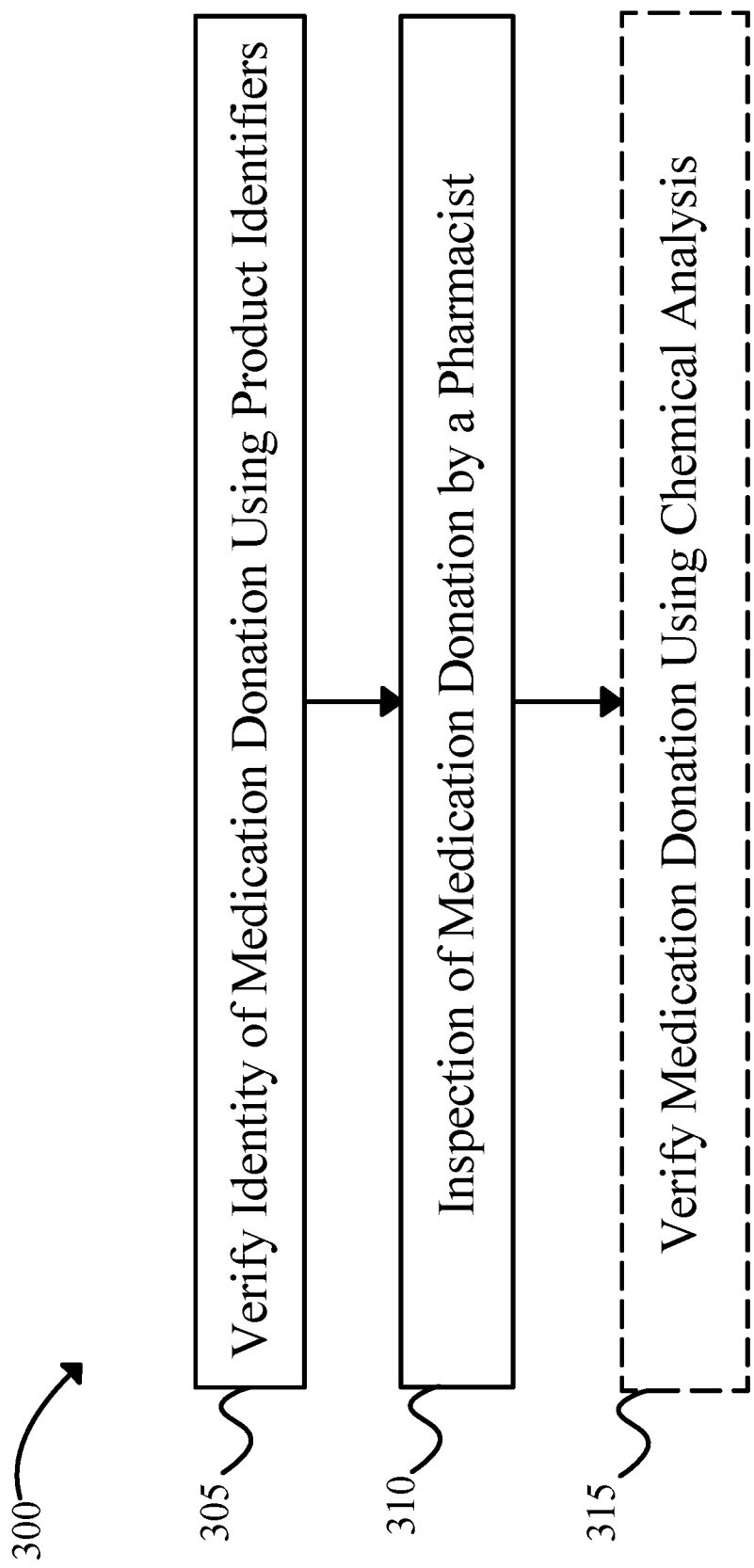
FIG. 3 is a flow chart of an exemplary method for verifying medication donations.

Now referring to FIG. 3, a flow chart for an exemplary method 300 for verifying the medication donation is shown. In some embodiments, method 300 may include any of the medication donation verification methods disclosed with reference to FIG. 1. Method 300 may include a step 305 of verifying the donated medication using product identifiers. For the purposes of this disclosure, a "product identifier" is a piece of information that identifies the medication contained in a medication donation. Product identifier may include, product codes, product names, trademarks, brand names, serial numbers, identification numbers, barcodes, and the like. In some embodiments, step 305 may be carried out manually by a person or team of people. In some embodiments, step 305 may be carried out at least in part by using a machine learning model, such as identification machine learning model disclosed in this disclosure. In some embodiments, step 305 may include the use of OCR, or an image classifier as disclosed in this disclosure.

With continued reference to FIG. 3, method 300 may further include a step 310 of inspection of the medication donation by a pharmacist. The pharmacist may be consistent with any other pharmacist disclosed as part of this disclosure. In some embodiments, the pharmacist could be a registered pharmacist (RPh). As a non-limiting example, the pharmacist may inspect each pill in medication donation, including by visual inspection, verify the drug identity of the medicine in medication donation, verify the dosage of the medicine in medication donation, verify the drug expiration date, and/or certify the intact tamper evident seals.

With continued reference to FIG. 3, method 300 may further include a step 315 of verifying the medication donation using chemical analysis. In some embodiments, this step 315 may be optional. Particularly, in various embodiments, step 315 may be performed for a random selection of medication donation. As a non-limiting example, this may be accomplished using the output of a random number generator. By changing what output from the random number generator causes the medication donation to undergo further verification testing, the probability of a given medication donation being selected can be adjusted. In some embodiments, step 315 may be performed for every $n^{th}$ medication donation, wherein n is an integer above zero. As a non-limiting example, where n=100 every $100^{th}$ medication donation may be selected to undergo step 315. In some embodiments, a statistically relevant sample of medication donations may be selected to undergo step 315. In some embodiments, step 315 may include sending the medication donation to a third-party chemical analytic company. The chemical analysis of step 315 may include any relevant chemical analysis technique known in the art. As a non-limiting example, the chemical analysis may include spectroscopy. As another non-limiting example, the chemical analysis may include mass spectroscopy. As another non-limiting example, the chemical analysis may include thermal analysis. In some embodiments, method 300 may be a proprietary three-step medication verification process.

Figure 4:
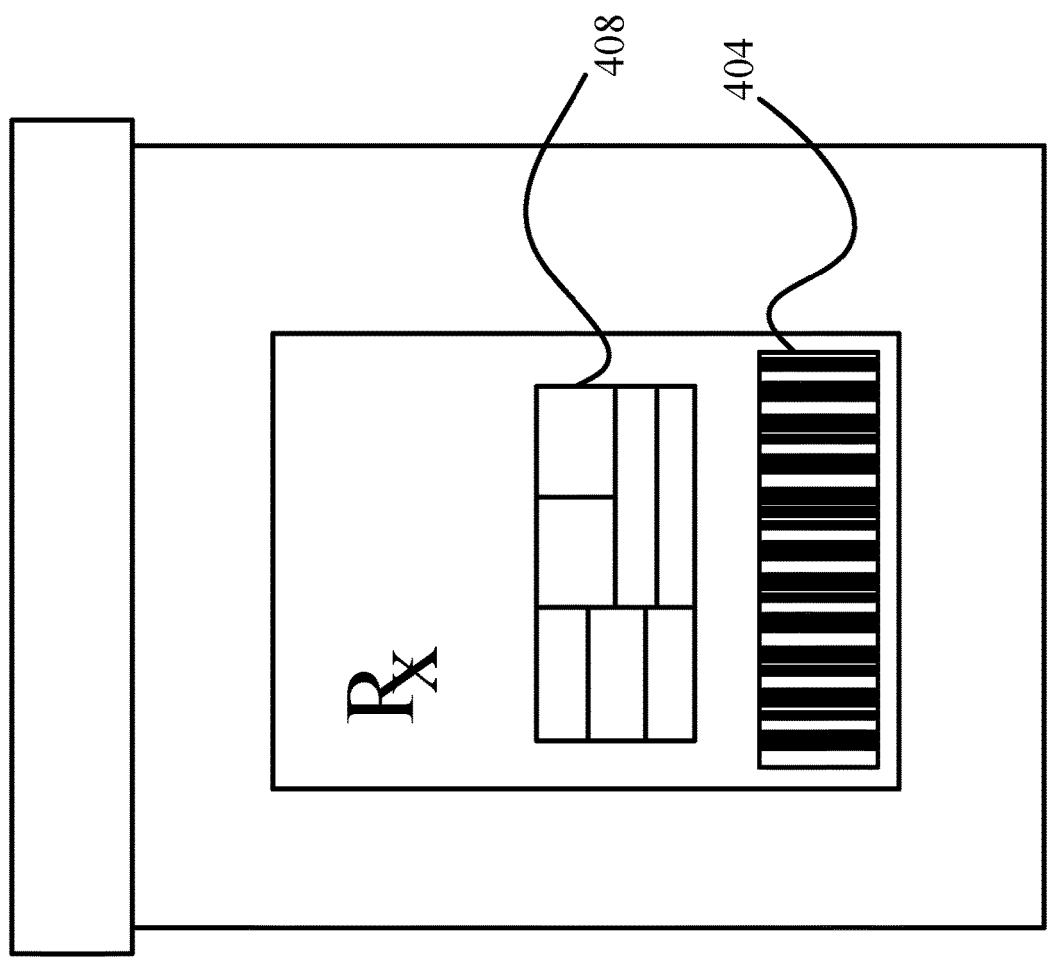
FIG. 4 is an illustration of exemplary packaging for a medication donation.

Referring now to FIG. 4, exemplary packaging 400 for a medication donation is shown. While exemplary packaging 400 is depicted in FIG. 4 as a bottle, in various embodiments, exemplary packaging 400 may include a syringe, bag, box, container, blister pack, and the like. In some embodiments, exemplary packaging 400 may include, as an example, a barcode 404. A "barcode," for the purposes of this disclosure is a non-textual pattern used to represent data in a machine-readable form. As a non-limiting example, barcode 404 may include a GS1 barcode, a QR code, a UPC code, an EAN code, a data matrix, and the like.

Continuing to refer to FIG. 4, exemplary packaging 400 may include a set of medication information 408. Medication information 408 may contain a variety of information regarding a medication donation. Medication information 408 may include, as a non-limiting example, the generic name for the medicine in medication donation, the quantity of medication in medication donation, the dosage of the medicine in medication donation, the source of the medicine in medication donation, the expiration date of the medicine in the medication donation, and the like. Medication information 408 may be presented in any logical format, including, as non-limiting examples, a table, a list, a matrix, and the like.

With continued reference to FIG. 4, actual medication information, as disclosed in this disclosure, may be collected, in some embodiments, from exemplary packaging. In some embodiment, this may be done using OCR as disclosed in this disclosure. In some embodiments, an image classifier may be used to collect actual medication information. In some embodiments, a machine learning model may be used to sort and identify the actual medication information from, for example, barcode 404 and medication information 408. In some embodiments, a machine vision system, such as the one described with reference to FIG. 1, may be used to process an image of any portion of exemplary packaging 400 to identify information from the image. For example, the machine vision system could identify barcode 404 or medication information 408. As a non-limiting example, the machine vision system could count the number of pills in a package.

Figure 5:
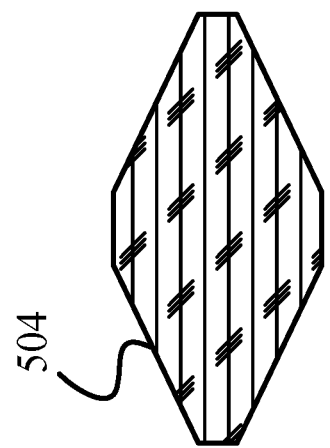
FIG. 5 is an illustration of an exemplary first medication pill and second medication pill.
Figure 5:
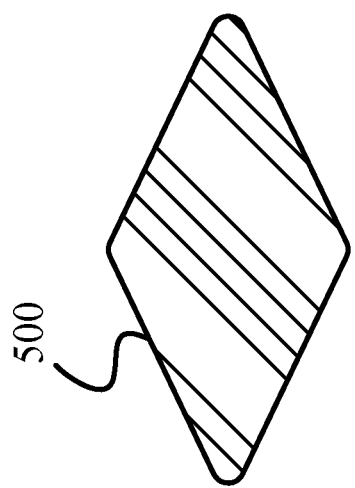

Referring now to FIG. 5, a first medication pill 500 and a second medication pill 504 are depicted. First medication pill 500 may have a different size or shape from second medication pill 504. In some embodiments, first medication pill 500 may have, for example, a different coating or texture from second medication pill 504; this is indicated by the different fill patterns in FIG. 5. In some embodiments, first medication pill 500 and/or second medication pill 504 may include unique identifiers, wherein the unique identifiers are alphanumeric strings imprinted or printed on first medication pill 500 and/or second medication pill 504. In some embodiments, an image classifier may be used to collect actual medication information from a first medication pill 500 and/or second medication pill 504, for example, using a picture of first medication pill 500. In some embodiments, a machine learning model may be used to collect actual medication information from first medication pill 500. The machine learning model may be trained on pictures or videos of various medication pills and the medication information corresponding to those medication pills. Using these techniques, first medication pill 500 can be differentiated from second medication pill 504 when collecting the actual medication information. In some embodiments, a machine vision system, such as the one described with reference to FIG. 1, may be used to process an image of first medication pill 500 and/or second medication pill 504 to identify information from the image. For example, the machine vision system could identify the size, shape, coating, texture, and/or unique identifier from first medication pill 500 and/or second medication pill 504.

Figure 6:
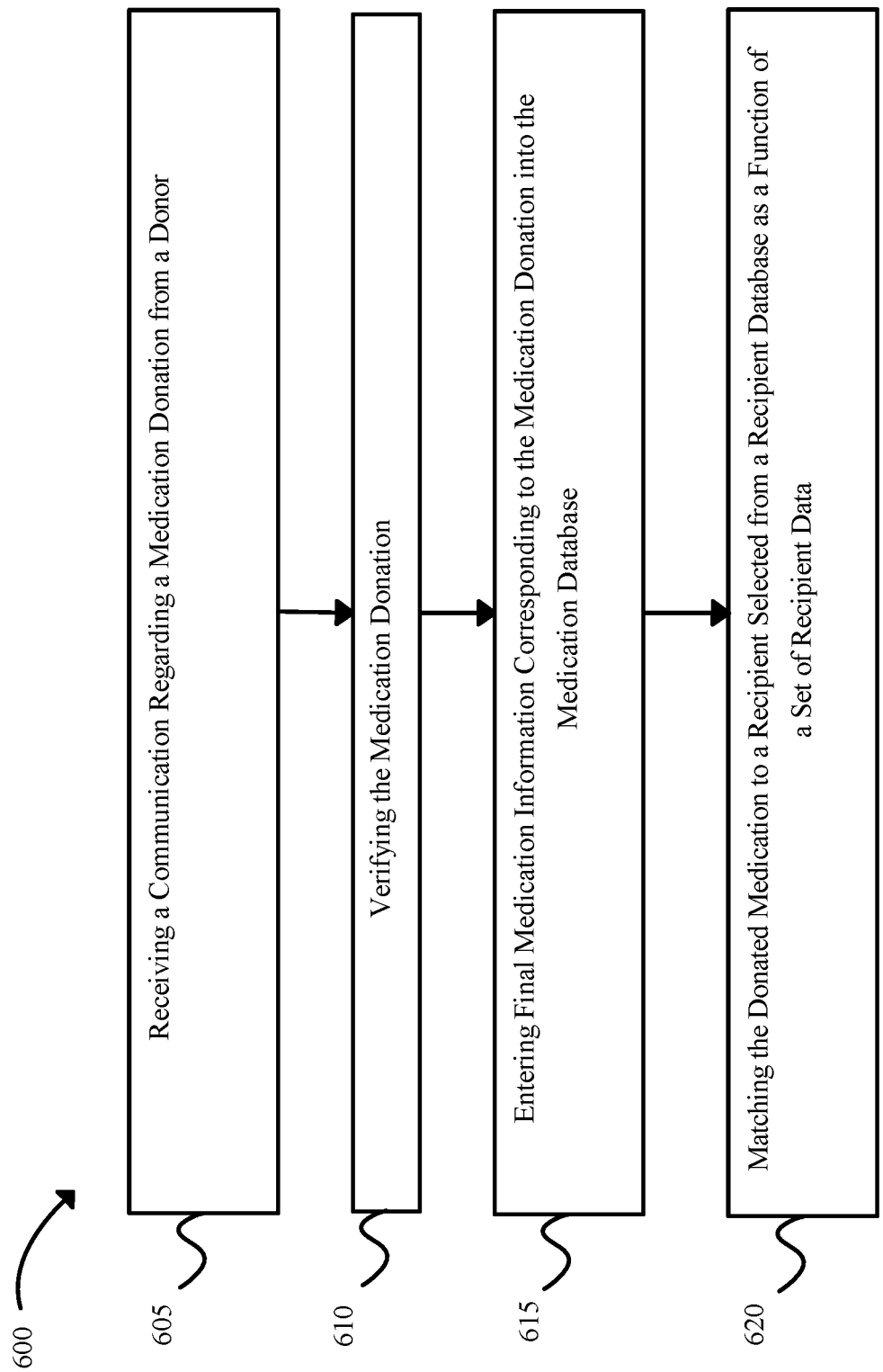
FIG. 6 is a flow chart for a method for redistributing medicine.

Referring now to FIG. 6, a method for redistributing medication 600 is shown. In some embodiments, method 600 may be performed by a computing device (e.g., computing device 104 discussed with reference to FIG. 1). Method 600 includes a step 605 of receiving a communication regarding a medication donation from a donor, wherein the communication includes donor medication information regarding the medication donation. The communication may be consistent with communication 108 discussed with reference to FIG. 1. Medication donation may be consistent with any medication donation disclosed as part of this disclosure. Donor medication information may be consistent with any donor medication information disclosed as part of this disclosure. Donor may be consistent with any donor disclosed as part of this disclosure. In some embodiments, a communication regarding a medication donation from a donor may comprise automatically generating a shipping label for the medication donation. The process of automatically generating a shipping label may be consistent with any process for automatically generating a shipping label disclosed in this disclosure. The shipping label may be consistent with any shipping label disclosed as part of this disclosure.

With continued reference to FIG. 6, method 600 further includes a step 610 of verifying the medication donation, wherein verifying the medication donation includes verifying the identity of the medication donation. Verifying the medication donation may be consistent with any process for verifying the medication donation disclosed as part of this disclosure. Verifying the identity of the medication donation may be consistent with any process for verifying the identity of the medication donation disclosed as part of this disclosure. In some embodiments, step 610 may further include verifying the integrity of the medication donation. Verifying the integrity of the medication donation may be consistent with any process for verifying the integrity of the medication donation disclosed as part of this disclosure. In some embodiments, step 610 may further include selecting, optionally, the medication donation for further donation. Selecting, optionally, the medication donation for further verification may be consistent with any process for selecting, optionally, the medication donation for further verification disclosed as part of this disclosure. In some embodiments, step 610 may further include creating a verification record including a verification status of the medication donation, wherein the verification record is stored using an immutable sequential listing. The verification record may be consistent with any verification record disclosed as part of this disclosure. The verification status of the medication donation may be consistent with any verification status of the medication donation disclosed as part of this disclosure. The immutable sequential listing may be consistent with any immutable sequential listing disclosed as part of this disclosure. Verifying the identity of the medication donation includes collecting actual medication information from the medication donation. The process of collecting actual medication information from the medication donation may be consistent with any process for collecting actual medication information disclosed as part of this disclosure. Actual medication information may be consistent with any actual medication information disclosed as part of this disclosure. Verifying the identity of the medication donation may also include using an identification machine learning model to verify the identity of the medication donation, wherein the identification machine learning model may be trained to verify the identity of the medication donation by comparing the donor medication information to the actual medication information. Identification machine learning model may be consistent with any identification machine learning model disclosed as part of this disclosure. In some embodiments, the step of collecting actual medication information may include using a sensor to collect actual medication information. The sensor may be consistent with any sensor disclosed as part of this disclosure; particularly sensor 144 in FIG. 1. In some embodiments, the sensor may include a camera. The camera may be consistent with any camera disclosed as part of this disclosure. In some embodiments, collecting actual medication information may include receiving an image of the medication donation from the camera and using an image classifier to classify the image. The image classifier may be consistent with any image classifier disclosed as part of this disclosure.

With continued reference to FIG. 6, method 600 further includes a step 615 of entering final medication information corresponding to the medication donation into the medication database. Final medication information may be consistent with any final medication information disclosed as part of this disclosure. Medication database may be consistent with any medication database disclosed as part of this disclosure.

With continued reference to FIG. 6, method 600 further includes a step 620 of matching the medication donation to a recipient selected from a recipient database as a function of a set of recipient data, wherein each recipient in the recipient database has an associated set of recipient data. The recipient may be consistent with any recipient disclosed as part of this disclosure. The recipient database may be consistent with any recipient database disclosed as part of this disclosure. Recipient data may be consistent with any recipient data disclosed as part of this disclosure. In some embodiments, step 620 may further include using a matching machine learning model to match the medication donation to a recipient from the recipient database, wherein the matching machine learning model that takes the final medication information from the medication database as input and outputs at least a recipient from the recipient database. Matching machine learning model may be consistent with any matching machine learning model disclosed as part of this disclosure.

With continued reference to FIG. 6, method 600 may further include removing the medication donation information corresponding to a medication donation from the medication database when a buffer time period before an expiration date of the medication donation is reached. The buffer time period may be consistent with any buffer time period disclosed as part of this disclosure. The expiration data of the medication donation may be consistent with any expiration data of the medication donation disclosed as part of this disclosure. In some embodiments, method 600 may further include verifying the identity of the donor using at least a donor credential from the donor. The process of verifying the identity of the donor may be consistent with any process of verifying the identity of the donor disclosed as part of this disclosure. The donor credential may be consistent with donor credential 136 discussed with reference to FIG. 1. In some embodiments, method 600 may further include identifying a central repository to store the medical donation. The process for identifying a central repository to store the medical donation may be consistent with any process for identifying a central repository to store the medical donation disclosed as part of this disclosure. Central repository may be consistent with any central repository disclosed as part of this disclosure.

Figure 7:
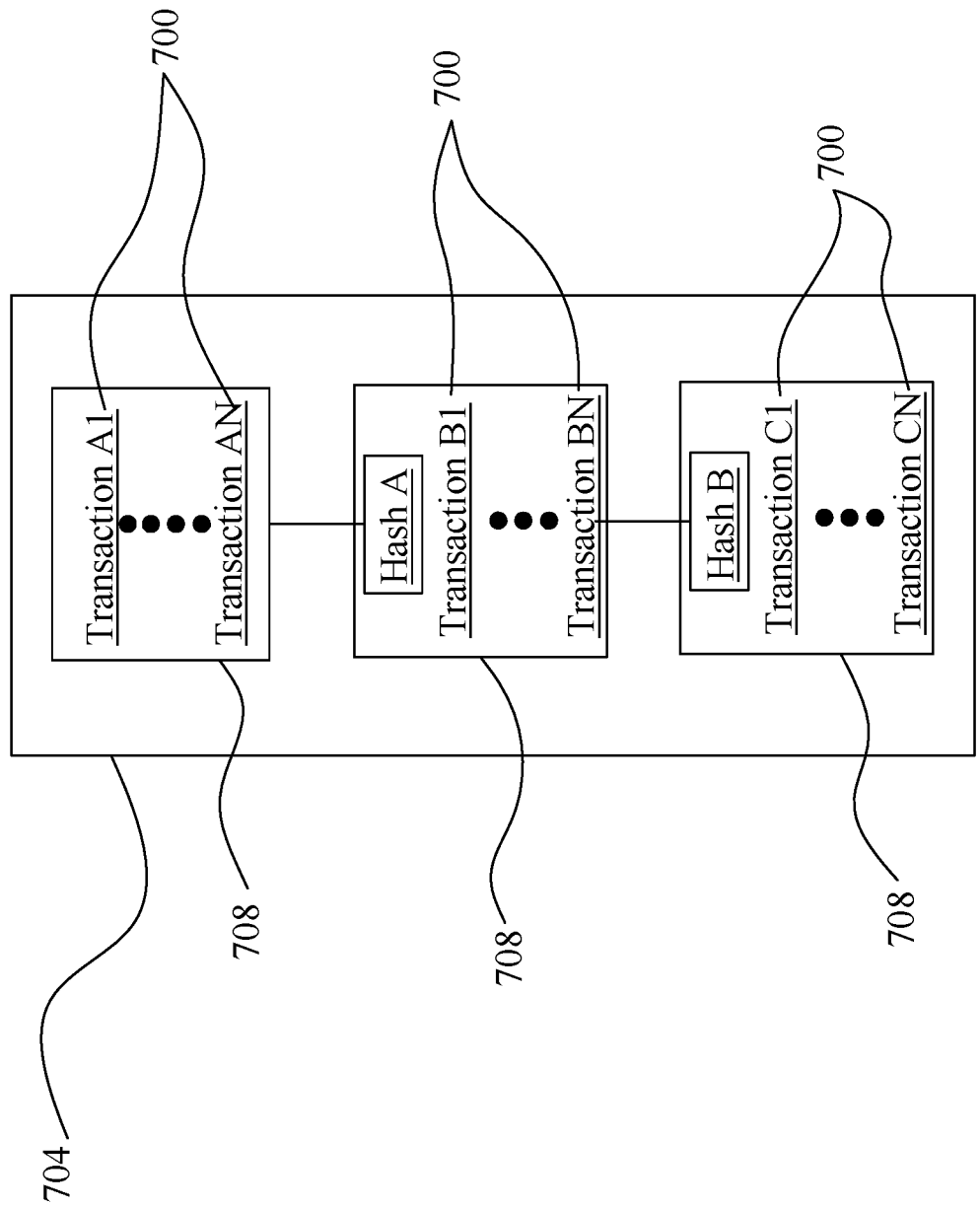
FIG. 7 is a diagram of an exemplary embodiment of an immutable sequential listing.

Referring now to FIG. 7, an exemplary embodiment of an immutable sequential listing 700 is illustrated. Data elements are listing in immutable sequential listing 700; data elements may include any form of data, including textual data, image data, encrypted data, cryptographically hashed data, and the like. Data elements may include, without limitation, one or more at least a digitally signed assertion. In one embodiment, a digitally signed assertion 704 is a collection of textual data signed using a secure proof as described in further detail below; secure proof may include, without limitation, a digital signature as described above. Collection of textual data may contain any textual data, including without limitation American Standard Code for Information Interchange (ASCII), Unicode, or similar computer-encoded textual data, any alphanumeric data, punctuation, diacritical mark, or any character or other marking used in any writing system to convey information, in any form, including any plaintext or cyphertext data; in an embodiment, collection of textual data may be encrypted, or may be a hash of other data, such as a root or node of a Merkle tree or hash tree, or a hash of any other information desired to be recorded in some fashion using a digitally signed assertion 204. In an embodiment, collection of textual data states that the owner of a certain transferable item represented in a digitally signed assertion 204 register is transferring that item to the owner of an address. A digitally signed assertion 204 may be signed by a digital signature created using the private key associated with the owner's public key, as described above.

Still referring to FIG. 7, a digitally signed assertion 704 may describe a transfer of virtual currency, such as cryptocurrency as described below. The virtual currency may be a digital currency. Item of value may be a transfer of trust, for instance represented by a statement vouching for the identity or trustworthiness of the first entity. Item of value may be an interest in a fungible negotiable financial instrument representing ownership in a public or private corporation, a creditor relationship with a governmental body or a corporation, rights to ownership represented by an option, derivative financial instrument, commodity, debt-backed security such as a bond or debenture or other security as described in further detail below. A resource may be a physical machine e.g., a ride share vehicle or any other asset. A digitally signed assertion 704 may describe the transfer of a physical good; for instance, a digitally signed assertion 704 may describe the sale of a product. In some embodiments, a transfer nominally of one item may be used to represent a transfer of another item; for instance, a transfer of virtual currency may be interpreted as representing a transfer of an access right; conversely, where the item nominally transferred is something other than virtual currency, the transfer itself may still be treated as a transfer of virtual currency, having value that depends on many potential factors including the value of the item nominally transferred and the monetary value attendant to having the output of the transfer moved into a particular user's control. The item of value may be associated with a digitally signed assertion 204 by means of an exterior protocol, such as the COLORED COINS created according to protocols developed by The Colored Coins Foundation, the MASTERCOIN protocol developed by the Mastercoin Foundation, or the ETHEREUM platform offered by the Stiftung Ethereum Foundation of Baar, Switzerland, the Thunder protocol developed by Thunder Consensus, or any other protocol.

Still referring to FIG. 7, in one embodiment, an address is a textual datum identifying the recipient of virtual currency or another item of value in a digitally signed assertion 704. In some embodiments, address is linked to a public key, the corresponding private key of which is owned by the recipient of a digitally signed assertion 704. For instance, address may be the public key. Address may be a representation, such as a hash, of the public key. Address may be linked to the public key in memory of a computing device, for instance via a "wallet shortener" protocol. Where address is linked to a public key, a transferee in a digitally signed assertion 704 may record a subsequent a digitally signed assertion 704 transferring some or all of the value transferred in the first a digitally signed assertion 704 to a new address in the same manner. A digitally signed assertion 704 may contain textual information that is not a transfer of some item of value in addition to, or as an alternative to, such a transfer. For instance, as described in further detail below, a digitally signed assertion 704 may indicate a confidence level associated with a distributed storage node as described in further detail below.

In an embodiment, and still referring to FIG. 7 immutable sequential listing 700 records a series of at least a posted content in a way that preserves the order in which the at least a posted content took place. Temporally sequential listing may be accessible at any of various security settings; for instance, and without limitation, temporally sequential listing may be readable and modifiable publicly, may be publicly readable but writable only by entities and/or devices having access privileges established by password protection, confidence level, or any device authentication procedure or facilities described in this disclosure, or may be readable and/or writable only by entities and/or devices having such access privileges. Access privileges may exist in more than one level, including, without limitation, a first access level or community of permitted entities and/or devices having ability to read, and a second access level or community of permitted entities and/or devices having ability to write; first and second community may be overlapping or non-overlapping. In an embodiment, posted content and/or immutable sequential listing 700 may be stored as one or more zero knowledge sets (ZKS), Private Information Retrieval (PIR) structure, or any other structure that allows checking of membership in a set by querying with specific properties. Such database may incorporate protective measures to ensure that malicious actors may not query the database repeatedly in an effort to narrow the members of a set to reveal uniquely identifying information of a given posted content.

Still referring to FIG. 7, immutable sequential listing 700 may preserve the order in which the at least a posted content took place by listing them in chronological order; alternatively or additionally, immutable sequential listing 700 may organize digitally signed assertions 704 into sub-listings 708 such as "blocks" in a blockchain, which may be themselves collected in a temporally sequential order; digitally signed assertions 704 within a sub-listing 708 may or may not be temporally sequential. The ledger may preserve the order in which at least a posted content took place by listing them in sub-listings 708 and placing the sub-listings 708 in chronological order. The immutable sequential listing 700 may be a distributed, consensus-based ledger, such as those operated according to the protocols promulgated by Ripple Labs, Inc., of San Francisco, Calif., or the Stellar Development Foundation, of San Francisco, Calif., or of Thunder Consensus. In some embodiments, the ledger is a secured ledger; in one embodiment, a secured ledger is a ledger having safeguards against alteration by unauthorized parties. The ledger may be maintained by a proprietor, such as a system administrator on a server, that controls access to the ledger; for instance, the user account controls may allow contributors to the ledger to add at least a posted content to the ledger but may not allow any users to alter at least a posted content that have been added to the ledger. In some embodiments, ledger is cryptographically secured; in one embodiment, a ledger is cryptographically secured where each link in the chain contains encrypted or hashed information that makes it practically infeasible to alter the ledger without betraying that alteration has taken place, for instance by requiring that an administrator or other party sign new additions to the chain with a digital signature. Immutable sequential listing 700 may be incorporated in, stored in, or incorporate, any suitable data structure, including without limitation any database, datastore, file structure, distributed hash table, directed acyclic graph or the like. In some embodiments, the timestamp of an entry is cryptographically secured and validated via trusted time, either directly on the chain or indirectly by utilizing a separate chain. In one embodiment the validity of timestamp is provided using a time stamping authority as described in the RFC 3161 standard for trusted timestamps, or in the ANSI ASC x9.95 standard. In another embodiment, the trusted time ordering is provided by a group of entities collectively acting as the time stamping authority with a requirement that a threshold number of the group of authorities sign the timestamp.

In some embodiments, and with continued reference to FIG. 7, immutable sequential listing 700, once formed, may be inalterable by any party, no matter what access rights that party possesses. For instance, immutable sequential listing 700 may include a hash chain, in which data is added during a successive hashing process to ensure non-repudiation. Immutable sequential listing 700 may include a block chain.

In one embodiment, a block chain is immutable sequential listing 700 that records one or more new at least a posted content in a data item known as a sub-listing 708 or "block." An example of a block chain is the BITCOIN block chain used to record BITCOIN transactions and values. Sub-listings 708 may be created in a way that places the sub-listings 708 in chronological order and link each sub-listing 708 to a previous sub-listing 708 in the chronological order so that any computing device may traverse the sub-listings 708 in reverse chronological order to verify any at least a posted content listed in the block chain. Each new sub-listing 708 may be required to contain a cryptographic hash describing the previous sub-listing 708. In some embodiments, the block chain contains a single first sub-listing 708 sometimes known as a "genesis block."

Still referring to FIG. 7, the creation of a new sub-listing 708 may be computationally expensive; for instance, the creation of a new sub-listing 708 may be designed by a "proof of work" protocol accepted by all participants in forming the immutable sequential listing 700 to take a powerful set of computing devices a certain period of time to produce. Where one sub-listing 708 takes less time for a given set of computing devices to produce the sub-listing 708 protocol may adjust the algorithm to produce the next sub-listing 708 so that it will require more steps; where one sub-listing 708 takes more time for a given set of computing devices to produce the sub-listing 708 protocol may adjust the algorithm to produce the next sub-listing 708 so that it will require fewer steps. As an example, protocol may require a new sub-listing 708 to contain a cryptographic hash describing its contents; the cryptographic hash may be required to satisfy a mathematical condition, achieved by having the sub-listing 708 contain a number, called a nonce, whose value is determined after the fact by the discovery of the hash that satisfies the mathematical condition. Continuing the example, the protocol may be able to adjust the mathematical condition so that the discovery of the hash describing a sub-listing 708 and satisfying the mathematical condition requires more or less steps, depending on the outcome of the previous hashing attempt. Mathematical condition, as an example, might be that the hash contains a certain number of leading zeros and a hashing algorithm that requires more steps to find a hash containing a greater number of leading zeros, and fewer steps to find a hash containing a lesser number of leading zeros. In some embodiments, production of a new sub-listing 708 according to the protocol is known as "mining." The creation of a new sub-listing 708 may be designed by a "proof of stake" protocol as will be apparent to those skilled in the art upon reviewing the entirety of this disclosure.

Continuing to refer to FIG. 7, in some embodiments, protocol also creates an incentive to mine new sub-listings 708. The incentive may be financial; for instance, successfully mining a new sub-listing 708 may result in the person or entity that mines the sub-listing 708 receiving a predetermined amount of currency. The currency may be fiat currency. Currency may be cryptocurrency as defined below. In other embodiments, incentive may be redeemed for particular products or services; the incentive may be a gift certificate with a particular business, for instance. In some embodiments, incentive is sufficiently attractive to cause participants to compete for the incentive by trying to race each other to the creation of sub-listings 708 Each sub-listing 708 created in immutable sequential listing 700 may contain a record or at least a posted content describing one or more addresses that receive an incentive, such as virtual currency, as the result of successfully mining the sub-listing 708.

With continued reference to FIG. 7, where two entities simultaneously create new sub-listings 708, immutable sequential listing 700 may develop a fork; protocol may determine which of the two alternate branches in the fork is the valid new portion of the immutable sequential listing 700 by evaluating, after a certain amount of time has passed, which branch is longer. "Length" may be measured according to the number of sub-listings 708 in the branch. Length may be measured according to the total computational cost of producing the branch. Protocol may treat only at least a posted content contained the valid branch as valid at least a posted content. When a branch is found invalid according to this protocol, at least a posted content registered in that branch may be recreated in a new sub-listing 708 in the valid branch; the protocol may reject "double spending" at least a posted content that transfer the same virtual currency that another at least a posted content in the valid branch has already transferred. As a result, in some embodiments the creation of fraudulent at least a posted content requires the creation of a longer immutable sequential listing 700 branch by the entity attempting the fraudulent at least a posted content than the branch being produced by the rest of the participants; as long as the entity creating the fraudulent at least a posted content is likely the only one with the incentive to create the branch containing the fraudulent at least a posted content, the computational cost of the creation of that branch may be practically infeasible, guaranteeing the validity of all at least a posted content in the immutable sequential listing 700.

Still referring to FIG. 7, additional data linked to at least a posted content may be incorporated in sub-listings 708 in the immutable sequential listing 700; for instance, data may be incorporated in one or more fields recognized by block chain protocols that permit a person or computer forming a at least a posted content to insert additional data in the immutable sequential listing 700. In some embodiments, additional data is incorporated in an unspendable at least a posted content field. For instance, the data may be incorporated in an OP_RETURN within the BITCOIN block chain. In other embodiments, additional data is incorporated in one signature of a multi-signature at least a posted content. In an embodiment, a multi-signature at least a posted content is at least a posted content to two or more addresses. In some embodiments, the two or more addresses are hashed together to form a single address, which is signed in the digital signature of the at least a posted content. In other embodiments, the two or more addresses are concatenated. In some embodiments, two or more addresses may be combined by a more complicated process, such as the creation of a Merkle tree or the like. In some embodiments, one or more addresses incorporated in the multi-signature at least a posted content are typical crypto-currency addresses, such as addresses linked to public keys as described above, while one or more additional addresses in the multi-signature at least a posted content contain additional data related to the at least a posted content; for instance, the additional data may indicate the purpose of the at least a posted content, aside from an exchange of virtual currency, such as the item for which the virtual currency was exchanged. In some embodiments, additional information may include network statistics for a given node of network, such as a distributed storage node, e.g. the latencies to nearest neighbors in a network graph, the identities or identifying information of neighboring nodes in the network graph, the trust level and/or mechanisms of trust (e.g. certificates of physical encryption keys, certificates of software encryption keys, (in non-limiting example certificates of software encryption may indicate the firmware version, manufacturer, hardware version and the like), certificates from a trusted third party, certificates from a decentralized anonymous authentication procedure, and other information quantifying the trusted status of the distributed storage node) of neighboring nodes in the network graph, IP addresses, GPS coordinates, and other information informing location of the node and/or neighboring nodes, geographically and/or within the network graph. In some embodiments, additional information may include history and/or statistics of neighboring nodes with which the node has interacted. In some embodiments, this additional information may be encoded directly, via a hash, hash tree or other encoding.

With continued reference to FIG. 7, in some embodiments, virtual currency is traded as a crypto currency. In one embodiment, a crypto currency is a digital, currency such as Bitcoins, Peercoins, Namecoins, and Litecoins. Crypto-currency may be a clone of another crypto-currency. The crypto-currency may be an "alt-coin." Crypto-currency may be decentralized, with no particular entity controlling it; the integrity of the crypto-currency may be maintained by adherence by its participants to established protocols for exchange and for production of new currency, which may be enforced by software implementing the crypto-currency. Crypto currency may be centralized, with its protocols enforced or hosted by a particular entity. For instance, crypto currency may be maintained in a centralized ledger, as in the case of the XRP currency of Ripple Labs, Inc., of San Francisco, Calif. In lieu of a centrally controlling authority, such as a national bank, to manage currency values, the number of units of a particular crypto-currency may be limited; the rate at which units of crypto-currency enter the market may be managed by a mutually agreed-upon process, such as creating new units of currency when mathematical puzzles are solved, the degree of difficulty of the puzzles being adjustable to control the rate at which new units enter the market. Mathematical puzzles may be the same as the algorithms used to make productions of sub-listings 708 in a block chain computationally challenging; the incentive for producing sub-listings 708 may include the grant of new crypto currency to the miners. Quantities of crypto currency may be exchanged using at least a posted content as described above.

Figure 8:
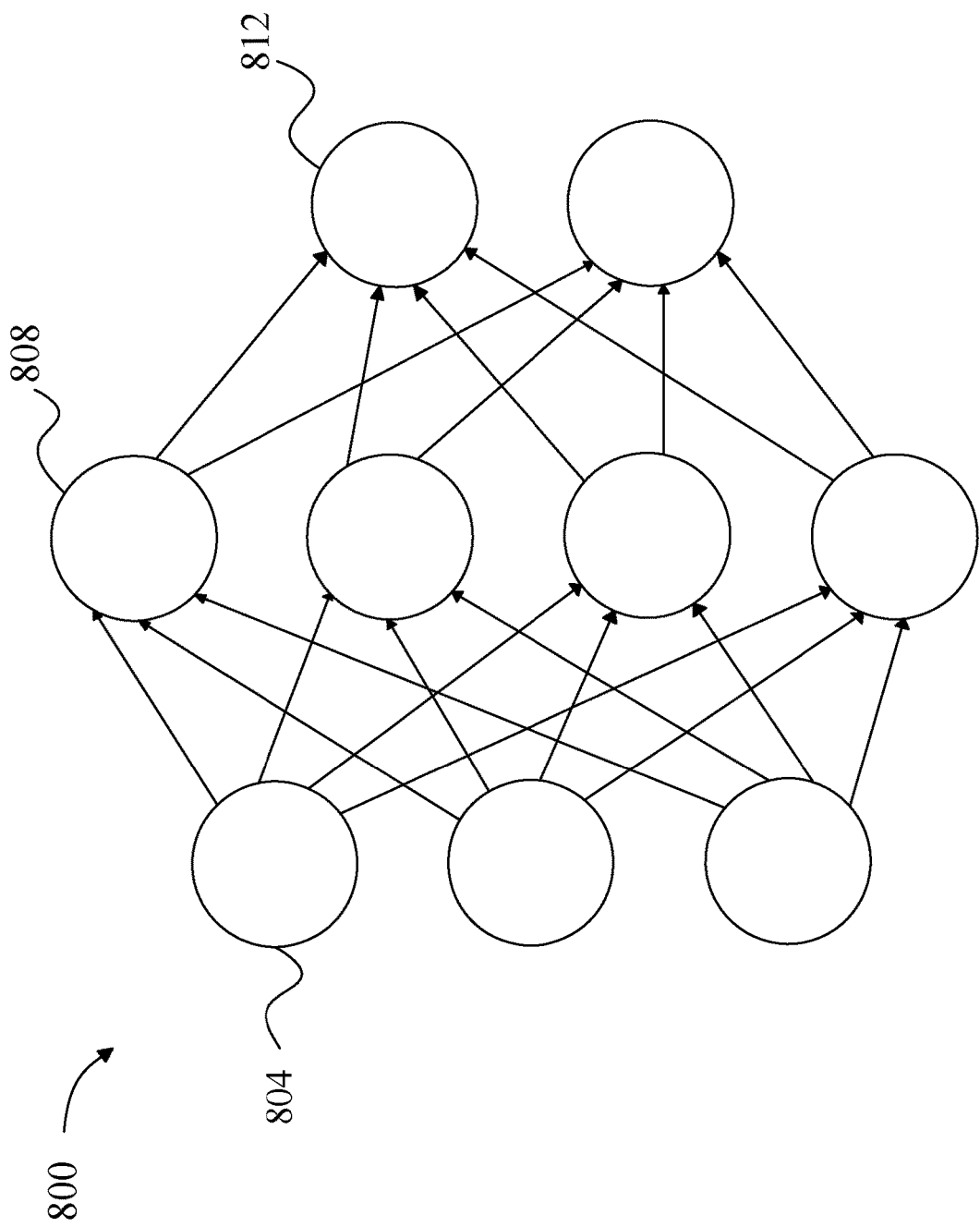
FIG. 8 is a diagram of an exemplary neural network.

Referring now to FIG. 8, an exemplary embodiment of neural network 800 is illustrated. A neural network 800 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 804, one or more intermediate layers 808, and an output layer of nodes 812. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network."

Figure 9:
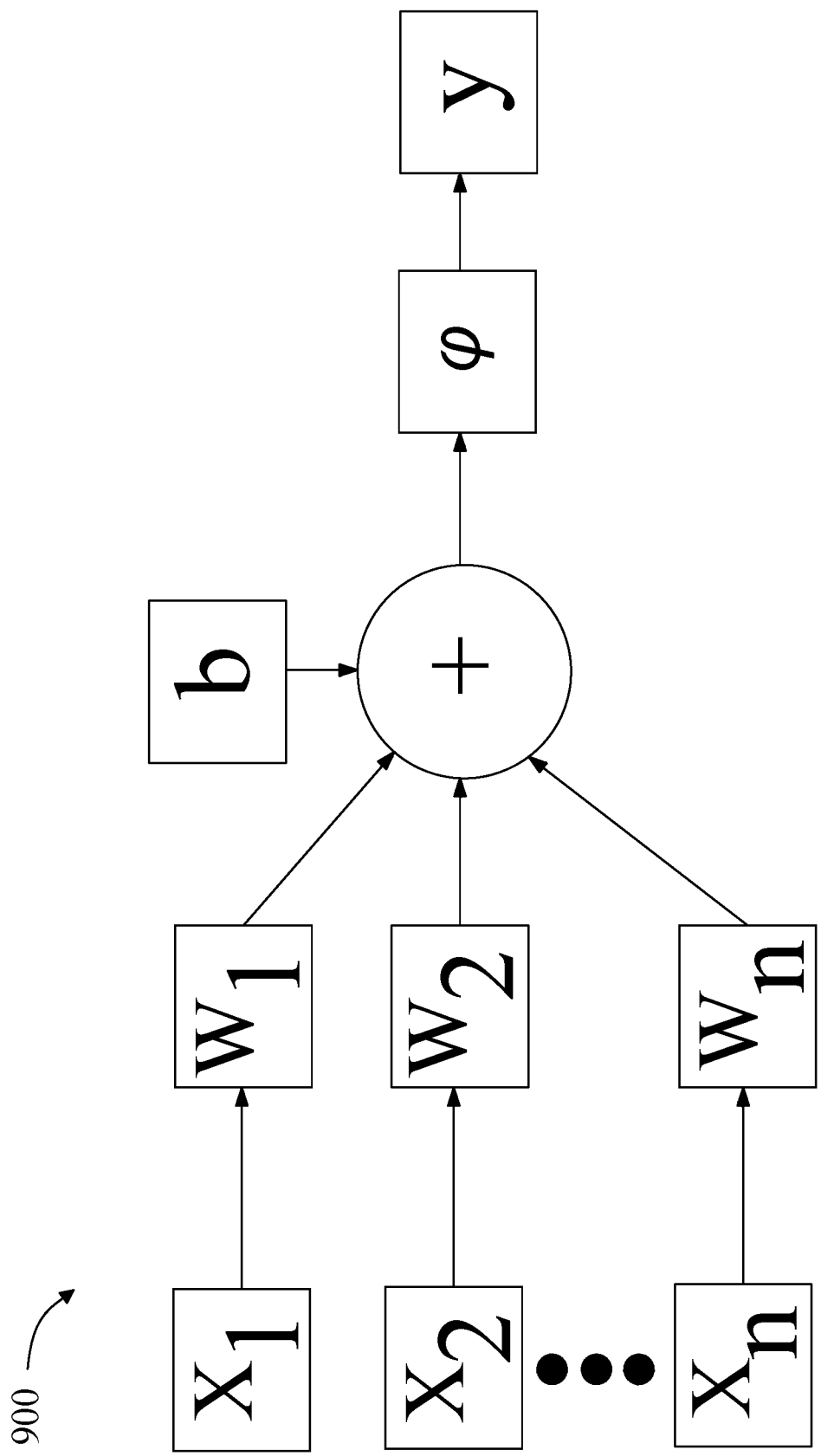
FIG. 9 is a diagram of an exemplary node of a neural network.

Referring now to FIG. 9, an exemplary embodiment of a node of a neural network 900 is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 10:
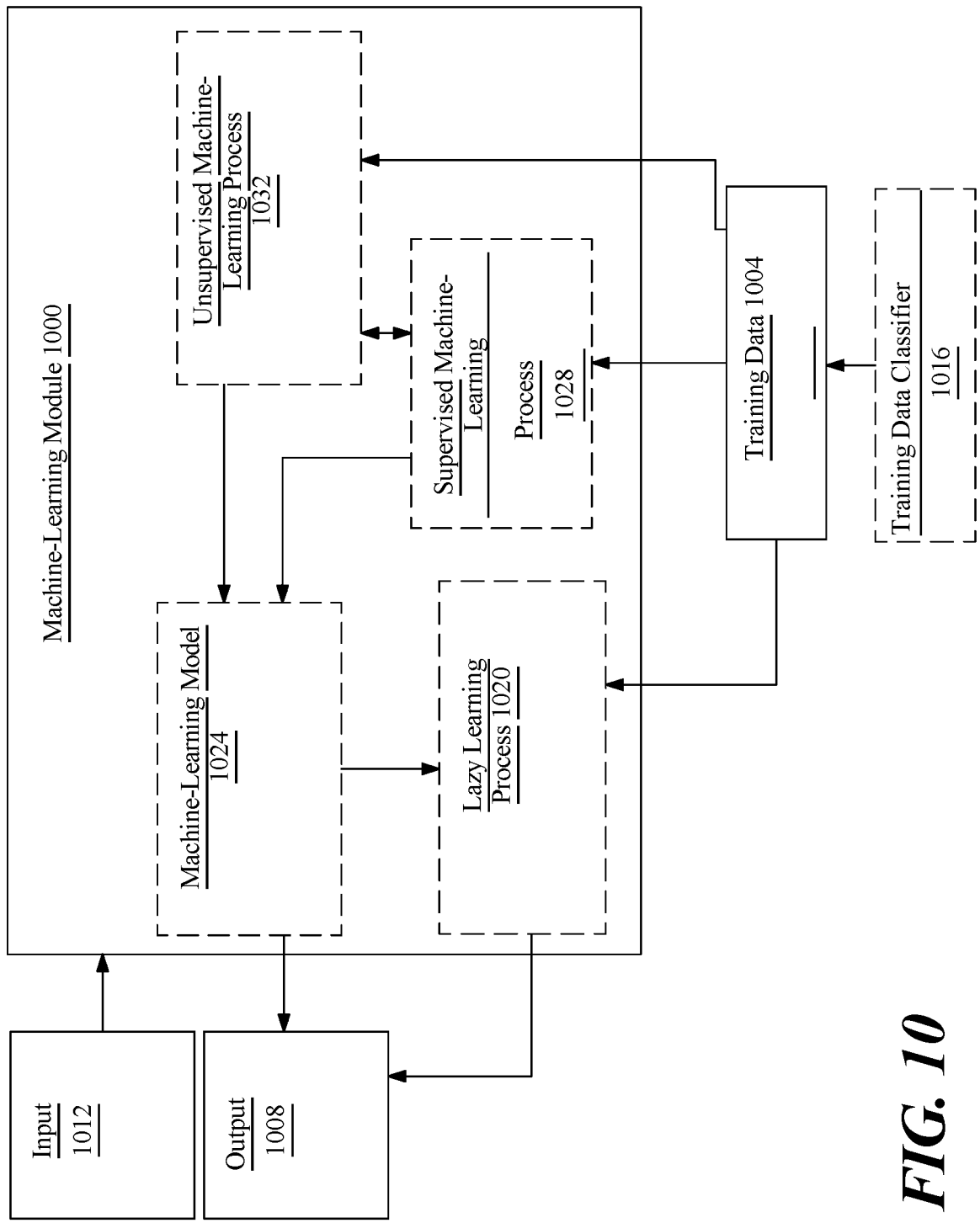
FIG. 10 is a diagram of an exemplary machine learning module.

Referring now to FIG. 10, an exemplary embodiment of a machine-learning module 1000 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 1004 to generate an algorithm that will be performed by a computing device/module to produce outputs 1008 given data provided as inputs 1012; this is in contrast to a non-machine learning software program where the commands to be executed are determined in advance by a user and written in a programming language.

Still referring to FIG. 10, "training data," as used herein, is data containing correlations that a machine-learning process may use to model relationships between two or more categories of data elements. For instance, and without limitation, training data 1004 may include a plurality of data entries, each entry representing a set of data elements that were recorded, received, and/or generated together; data elements may be correlated by shared existence in a given data entry, by proximity in a given data entry, or the like. Multiple data entries in training data 1004 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 1004 according to various correlations; correlations may indicate causative and/or predictive links between categories of data elements, which may be modeled as relationships such as mathematical relationships by machine-learning processes as described in further detail below. Training data 1004 may be formatted and/or organized by categories of data elements, for instance by associating data elements with one or more descriptors corresponding to categories of data elements. As a non-limiting example, training data 1004 may include data entered in standardized forms by persons or processes, such that entry of a given data element in a given field in a form may be mapped to one or more descriptors of categories. Elements in training data 1004 may be linked to descriptors of categories by tags, tokens, or other data elements; for instance, and without limitation, training data 1004 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 10, training data 1004 may include one or more elements that are not categorized; that is, training data 1004 may not be formatted or contain descriptors for some elements of data. Machine-learning algorithms and/or other processes may sort training data 1004 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 1004 to be made applicable for two or more distinct machine-learning algorithms as described in further detail below. Training data 1004 used by machine-learning module 1000 may correlate any input data as described in this disclosure to any output data as described in this disclosure.

Further referring to FIG. 10, training data may be filtered, sorted, and/or selected using one or more supervised and/or unsupervised machine-learning processes and/or models as described in further detail below; such models may include without limitation a training data classifier 1016. Training data classifier 1016 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 1000 may generate a classifier using a classification algorithm, defined as a process whereby a computing device and/or any module and/or component operating thereon derives a classifier from training data 1004. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 1016 may classify elements of training data to types of donors, types of recipients, types of medication, types of information, and the like.

Still referring to FIG. 10, machine-learning module 1000 may be configured to perform a lazy-learning process 1020 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1004. Heuristic may include selecting some number of highest-ranking associations and/or training data 1004 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 10, machine-learning processes as described in this disclosure may be used to generate machine-learning models 1024. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 1024 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1024 may be generated by creating an artificial neural network, such as a convolutional neural network including an input layer of nodes, one or more intermediate layers, and an output layer of nodes. Connections between nodes may be created via the process of "training" the network, in which elements from a training data 1004 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 10, machine-learning algorithms may include at least a supervised machine-learning process 1028. At least a supervised machine-learning process 1028, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 1004. Persons skilled in the art, upon reviewing the entirety of this disclosure, will be aware of various possible variations of at least a supervised machine-learning process 1028 that may be used to determine relation between inputs and outputs. Supervised machine-learning processes may include classification algorithms as defined above.

Further referring to FIG. 10, machine learning processes may include at least an unsupervised machine-learning processes 1032. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 10, machine-learning module 1000 may be designed and configured to create a machine-learning model 1024 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 10, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
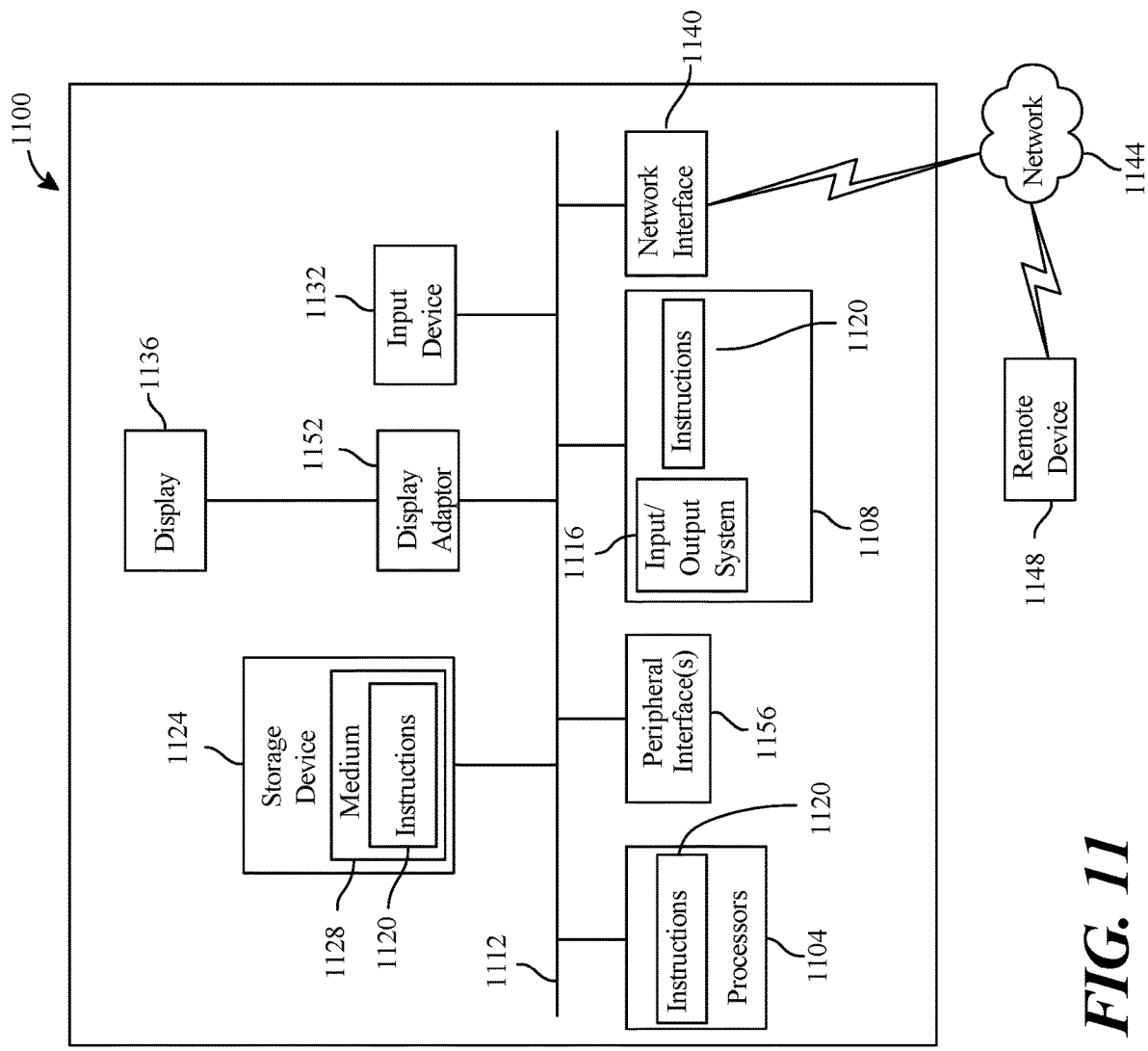
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for redistributing medication, the system comprising a computing device designed and configured to:
   receive a communication regarding a medication donation from a donor, wherein the communication comprises donor medication information regarding the medication donation;
   verify the medication donation, wherein verifying the medication donation comprises verifying the identity of the medication donation, wherein verifying the identity of the medication donation comprises collecting actual medication information from the medication donation using a sensor, wherein collecting the actual medication information further comprises:
      training, iteratively, an image classifying machine learning model using training data and a machine learning algorithm, wherein the training data comprises medication image data correlated with medication information data;
      capturing an image of the medication donation using the sensor; and
      generating the actual medication information for the medication donation using the trained image classifying machine learning model, wherein generating the actual medication information comprises providing the image of the medication donation as an input, to the trained image classifying machine learning model, to output, from the trained image classifying machine learning model, the actual medication information for the medication donation;
   enter final medication information corresponding to the medication donation into a medication database, wherein the final medication information comprises at least the actual medication information; and
   match the medication donation to a recipient selected from a recipient database as a function of the final medication information and a set of recipient data, wherein each recipient in the recipient database has an associated set of recipient data.

2. The system of claim 1, wherein matching the medication donation to the recipient selected from the recipient database comprises using a matching machine learning model to match the medication donation to the recipient from the recipient database, wherein the matching machine learning model takes the final medication information from the medication database as input and outputs the recipient from the recipient database.

3. The system of claim 1, wherein the sensor includes a camera, and wherein using the sensor comprises receiving the image of the medication donation from the camera, and using the image classifying machine learning model to classify the image.

4. The system of claim 1, wherein verifying the medication donation further comprises:
   using an identification machine learning model to verify the identity of the medication donation, wherein the identification machine learning model is trained to verify the identity of the medication donation by comparing the donor medication information to the actual medication information; and
   verifying the integrity of the medication donation.

5. The system of claim 1, wherein the computing device is further designed and configured to:
   remove the final medication donation information corresponding to the medication donation from the medication database when a buffer time period before an expiration date of the medication donation is reached.

6. The system of claim 1, wherein verifying the medication donation further comprises selecting, optionally, the medication donation for further verification testing.

7. The system of claim 1, wherein the computing device is further designed and configured to verify the identity of the donor using at least a donor credential from the donor.

8. The system of claim 1, wherein the computing device is further designed and configured to identify a central repository to store the medical donation.

9. The system of claim 1, wherein verifying the medication donation further comprises creating a verification record comprising a verification status of the medication donation, wherein the verification record is stored using an immutable sequential listing.

10. The system of claim 1, wherein verifying the medication donation further comprises verifying the medication donation as a function of a chemical analysis.

11. A method for redistributing medication, the method comprising:
   receiving a communication regarding a medication donation from a donor, wherein the communication comprises donor medication information regarding the medication donation;
   verifying the medication donation, wherein verifying the medication donation comprises verifying the identity of the medication donation, wherein verifying the identity of the medication donation comprises collecting actual medication information from the medication donation using a sensor, wherein collecting the actual medication information further comprises:
  training, iteratively, an image classifying machine learning model using training data and a machine learning algorithm, wherein the training data comprises medication image data correlated with medication information data;
  capturing an image of the medication donation using the sensor; and
  generating the actual medication information for the medication donation using the trained image classifying machine learning model, wherein generating the actual medication information comprises providing the image of the medication donation as an input, to the trained image classifying machine learning model, to output, from the trained image classifying machine learning model, the actual medication information for the medication donation;
entering final medication information corresponding to the medication donation into a medication database, wherein the final medication information comprises at least the actual medication information; and
matching the medication donation to a recipient selected from a recipient database as a function of the final medication information and a set of recipient data, wherein each recipient in the recipient database has an associated set of recipient data.

12. The method of claim 11, wherein matching the medication donation to the recipient selected from the recipient database comprises using a matching machine learning model to match the medication donation to the recipient from the recipient database, wherein the matching machine learning model takes the final medication information from the medication database as input and outputs the recipient from the recipient database.

13. The method of claim 11, wherein the sensor includes a camera, and wherein using the sensor comprises receiving the image of the medication donation from the camera and using the image classifying machine learning model to classify the image.

14. The method of claim 11, wherein verifying the medication donation further comprises:
  using an identification machine learning model to verify the identity of the medication donation, wherein the identification machine learning model is trained to verify the identity of the medication donation by comparing the donor medication information to the actual medication information; and
  verifying the integrity of the medication donation.

15. The method of claim 11, further comprising removing the final medication donation information corresponding to the medication donation from the medication database when a buffer time period before an expiration date of the medication donation is reached.

16. The method of claim 11, wherein verifying the medication donation further comprises selecting, optionally, the medication donation for further verification.

17. The method of claim 11, further comprising verifying the identity of the donor using at least a donor credential from the donor.

18. The method of claim 11, further comprising identifying a central repository to store the medical donation.

19. The method of claim 11, wherein verifying the medication donation further comprises creating a verification record comprising a verification status of the medication donation, wherein the verification record is stored using an immutable sequential listing.

20. The method of claim 11, wherein verifying the medication donation further comprises verifying the medication donation as a function of a chemical analysis.

\* \* \* \* \*